United States Patent
Lintner

(10) Patent No.: US 7,977,308 B2
(45) Date of Patent: Jul. 12, 2011

(54) LYS-THR DIPEPTIDES AND THEIR USE

(75) Inventor: Karl Lintner, Rambouillet (FR)

(73) Assignee: Sederma (FR)

( * ) Notice: Subject to any disclaimer, the term of this patent is extended or adjusted under 35 U.S.C. 154(b) by 379 days.

(21) Appl. No.: 11/919,539

(22) PCT Filed: Apr. 27, 2005

(86) PCT No.: PCT/IB2005/001821
§ 371 (c)(1),
(2), (4) Date: Oct. 26, 2007

(87) PCT Pub. No.: WO2006/114657
PCT Pub. Date: Nov. 2, 2006

(65) Prior Publication Data
US 2009/0029926 A1    Jan. 29, 2009

(51) Int. Cl.
*A61K 38/17* (2006.01)
(52) U.S. Cl. ...................................................... 514/2.2
(58) Field of Classification Search ........................ None
See application file for complete search history.

(56) References Cited

U.S. PATENT DOCUMENTS

2004/0063628 A1*  4/2004  Piccariello et al. ............. 514/12

FOREIGN PATENT DOCUMENTS

| CA | 2 465 123 A1 | 5/2003 |
| WO | WO-03/037933 A2 | 5/2003 |

OTHER PUBLICATIONS

Patent Abstract of Japan, vol. 2003, No. 12, & JP 2003 344416 A (National Institute of Advanced Industrial & Technology), Dec. 3, 2003.
Morozova et al., "Synthesis of a fragment of a polymyxin M lysine analog", Zhurnal Obshchei Khimii, vol. 37, No. 8, pp. 1764-1766, Aug. 1967.
Isshiki, "Enzymic hydrolysis of cycli peptides I. Enzymic cleavage og colistin", vol. 11, pp. 210-214, 1962.
Silaev, "Chemistry of polymyxin M. IV Synthesis and properties of possible fragments of polymyxin M", Zhurnal Obshchei Khitmii, vol. 31, 1961.
International Search Report, PCT/IB2005/001821, dated Dec. 1, 2005.

* cited by examiner

*Primary Examiner* — Brian-Yong S Kwon
*Assistant Examiner* — Lyndsey Beckhardt
(74) *Attorney, Agent, or Firm* — Lerner, David, Littenberg, Krumholz & Mentlik, LLP

(57) ABSTRACT

Dipeptides and derivatives and analogs, such as Pal-KT have been developed. These dipeptides, derivatives and analogs may be used alone or in an additive, to produce cosmetics, topical pharmaceuticals and personal care products, particularly for skin care. Methods of making the dipeptides, derivatives, analogs and additives containing same are also described.

5 Claims, No Drawings

LYS-THR DIPEPTIDES AND THEIR USE

BACKGROUND OF THE INVENTION

Our skin is the first image each of us offers to those who behold us. From time immemorial, the appearance of the skin has been a subject of preoccupation.

Our current knowledge of the physiology of the skin now enables us to propose cosmetic solutions to the various dysfunctions induced by external aggression and aging. However, many things remain poorly elucidated, poorly understood and poorly controlled.

This is true, for instance, in the case of the general symptoms of cutaneous aging, which give rise to wrinkles and flaccid and thin skin. The treatment of those symptoms is an important subject of research for the cosmetic market.

External or internal factors can both lead to the emergence of symptoms of aging. Moreover, as skin ages, the synthesis of collagen or other macromolecules in connective tissue is slowed; proteolysis, induced by solar radiation, is accelerated and the skin grows thinner and loses elasticity.

Numerous cosmetic compositions intended to improve the appearance of facial skin have been proposed to date. These include moisturizing products, anti-wrinkle creams and smoothing and soothing lotions. Frequently, however, those products have side effects, are associated with stability problems and/or do not make good their promise over time. This is, in particular, the case for formulae containing vitamins and plant extracts.

The present invention is designed to assist in resolving the esthetic problems posed by those aging symptoms and, preferably, to address the underlying problems.

CA 2,465,123 A1 to Ludin et al. discloses polypeptides of various lengths (page 4, lines 12-16) which are purportedly dermopharmaceutically and cosmetically active. The C terminal amino acid of many of these peptides is serine ("Ser"). Indeed, at page 5, lines 12-13, the '123 application discloses that the C terminal residue is "preferably derived from serine." Table 5 on page 20 of the '123 application and claims 15, 16 and 17 identify a number of peptides of varying sizes and compositions most of which bear serine or derivatives as the C terminal amino acid.

SUMMARY OF THE INVENTION

Irrespective of any possible advantage in other types and sizes of peptides, it has now been found, surprisingly, that C terminal serine residues yield dipeptides which may not be dermopharmaceutically and/or cosmetically active or which may not be useful in preferred applications. Indeed, it has been found that dipeptides including, for example, lysine and serine (Lys-Ser) have inadequate properties for many dermopharmaceutical and cosmetic applications. The fact that serine did not work made it surprising to discover that the use of threonine (Thr) as the C terminal residue in a dipeptide is particularly desirable, providing attributes far in excess of similar dipeptides terminating with a serine. The dipeptide Lys-Thr and N-acyl derivatives and esters, and nitrogen containing C terminal derivatives thereof can provide superior properties when compared to the corresponding Lys-Ser dipeptide.

The present invention therefore relates to a dipeptide where the C terminal amino acid is threonine ("Thr"). More preferably, the N terminal amino acid of such dipeptides is a basic amino acid, one which is positively charged at a pH of 6.0. These include the naturally occurring amino acids lysine (Lys), arginine (Arg) and histidine (His). Most preferred is the use of lysine. Thus, a particularly preferred dipeptide in accordance with the present invention has the sequence Lys-Thr and N-acyl derivatives and esters, and nitrogen containing C terminal derivatives thereof.

Dipeptides and derivatives in accordance with the present invention include, without limitation, His-Thr, Arg-Thr, Lys-Thr, Alk-His-Thr, Alk-Arg-Thr, Alk-Lys-Thr, His-Thr-OAlk, Arg-Thr-OAlk, Lys-Thr-OAlk, His-Thr-NR$_1$R$_2$, Arg-Thr-NR$_1$R$_2$, Lys-Thr-NR$_1$R$_2$, Alk-His-Thr-OAlk, Alk-Lys-Thr-NRR$_2$, Alk-Lys-Thr-OAlk. When used on the left side of the sequence "Alk" refers to an N-acyl derivative as defined herein. When used on the right side of the sequence, "OAlk" refers to an ester group attached to the C terminal carbonyl of Thr (e.g. COOAlk). "NR$_1$R$_2$" is as defined herein.

In another embodiment, the present invention relates to dipeptides having the following structure:

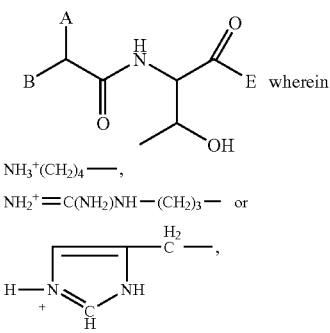 wherein $A = NH_3^+(CH_2)_4—$, $NH_2^+ = C(NH_2)NH—(CH_2)_3—$ or $$H—N^+{=}\!\!\!\!\!\!\!\!\stackrel{\phantom{X}}{\underset{H}{C}}\!\!\!\!\!\!\!\!—NH—\stackrel{H_2}{C}—,$$

B=—NH$_2$, —NH$_3^+$, —NH-D,

D=an acyl group of 2-22 carbon atoms in length, or biotinyl group, and

E=—O-Alk, —NR$_1$R$_2$, —H, —O$^-$, or —OH, wherein Alk is an alkyl group of 1-24 carbons in length, and R$_1$ and R$_2$ are independently H or an alkyl group of 1-12 carbons in length. In a particularly preferred embodiment, B=—NH-D, and more particularly, D is an acyl group of 2-22 carbons, and cosmetic and personal care products including same.

The dipeptides in accordance with the present invention, when provided in formulations, are. provided in an amount which is effective to treat at least one sign of skin aging. The phrase "to treat at least one sign of skin aging" as used herein means that the dipeptide provides an objectively measurable increase in its effect on some aspect of aging when used topically and applied to skin in need of treatment in an effective amount. This can be, for example, a greater reduction in wrinkles, increased potency, the ability to stimulate or inhibit at least one biochemical process within the skin to a greater degree, and the like. Generally, this is determined based on comparison to a control. However, particularly preferred formulations in accordance with the present invention will provide an objectively measurable increase in the effect on some aspect of aging when compared to the dipeptide Lys-Ser under similar conditions.

Formulations in accordance with the invention preferably require an "effective amount" of dipeptide. This amount of dipeptide may vary depending upon the type of product, which of the signs of aging are to be addressed and the like. Cosmetic, personal care and dermatological formulations including these dipeptides are all contemplated and include for example creams, gels, lotion bases, emulsions, colloids, ointments, milks, sprays and the like. These compositions or formulations of the invention also include, in addition to at least one dipeptide as defined herein, at least one additional ingredient.

The present invention also is directed to the use of such formulations for the protection of a medicament useful for the treatment of signs of skin aging and in particular wrinkles, as well as for methods of their use in various cosmetic and dermatological applications as well. In another embodiment, the present invention provides an additive for use in personal care products comprising: at least one dipeptide having the following structure

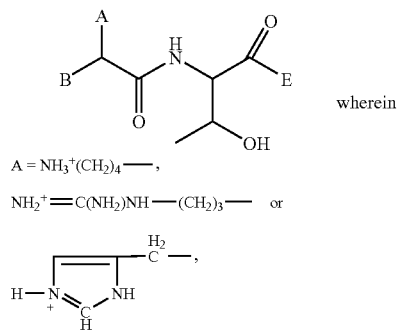

wherein $A = NH_3^+(CH_2)_4—$, $NH_2^+ = C(NH_2)NH—(CH_2)_3—$ or

[imidazole structure]

B=—NH$_2$, —NH$_3^+$, —NH-D,
D=an acyl group of 2-22 carbon atoms in length, or biotinyl group, and
E=—O-Alk, —NR$_1$R$_2$, —H, —O$^-$, or —OH,
wherein Alk is an alkyl group of 1-24 carbons in length, and R$_1$ and R$_2$ are independently H or an alkyl group of 1-12 carbons in length and at least one delivery agent. The delivery agent is generally selected and provided in an amount which is sufficient to solubilize, disburse, suspend, chelate, preserve, stabilize, structure, adjust the pH of, or protect from microbial attack said dipeptide. These additives can then be used in formulating personal care products, cosmetics and dermopharmaceuticals. In another embodiment, the additive consists essentially of dipeptides as described herein having the structure previously illustrated and at least one delivery agent.

DETAILED DESCRIPTION

All publications cited herein are hereby incorporated by reference in their entirety. Reference to a dipeptide in accordance with the present invention means a dipeptide whose C terminal amino acid is Thr. These include, unless the context specifies otherwise, N-acyl derivatives thereof, as well as C terminal derivatives such as esters, acid halides and nitrogen containing compounds as discussed herein.

The N-acyl derivatives are groups attached to the N terminal amino acid in place of a hydrogen and can include alkyl chains of carbon lengths of between 2 and 22. carbons. These can be linear or branched, substituted or unsubstituted, saturated or unsaturated, hydroxylated or not, containing sulfur or not. N-Acyl may also represent a biotinyl group. Similarly, the threonine may be in the form of a C terminal derivative including, for example, an acid, an ester with an alkyl chain having a carbon length of between 1 and 24 carbons ("Oalk"), preferably 1 to 3 carbons or 14 to 18 carbons. These can be linear or branched, substituted or unsubstituted, saturated or unsaturated, hydroxylated or not, containing sulfur or not. The C terminal derivative may also be NR$_1$R$_2$, in which R$_1$ and R$_2$ are independent of each other H or an alkyl chain of carbon length of between 1 and 12 carbons. These can be linear or branched, substituted or unsubstituted, saturated or unsaturated, hydroxylated or not, containing sulfur or not. Preferably, the acyl derivative attached to the N terminal amino acid is a palmitoyl group and most preferably, the C terminal amino acid is in the form of an acid. In accordance with another aspect of the present invention, dipeptides of the present invention have the following structure:

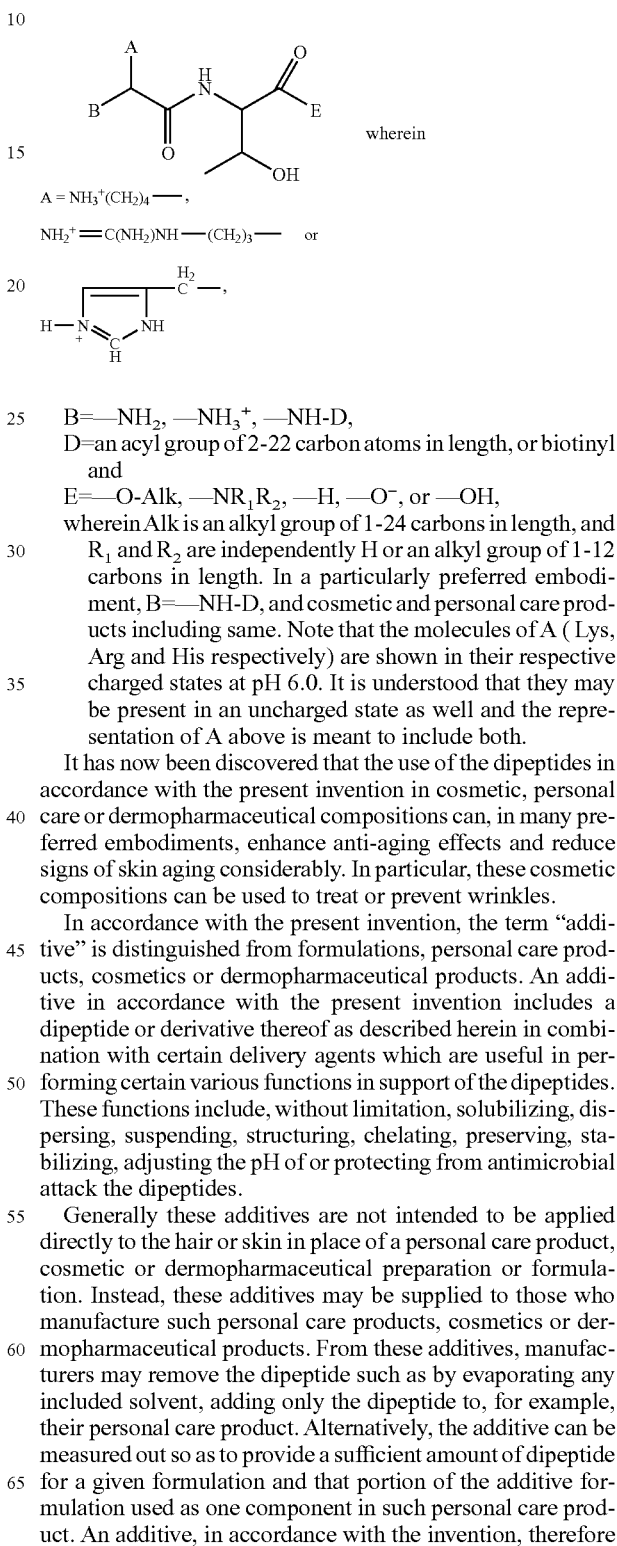

wherein $A = NH_3^+(CH_2)_4—$, $NH_2^+ = C(NH_2)NH—(CH_2)_3—$ or

[imidazole structure]

B=—NH$_2$, —NH$_3^+$, —NH-D,
D=an acyl group of 2-22 carbon atoms in length, or biotinyl and
E=—O-Alk, —NR$_1$R$_2$, —H, —O$^-$, or —OH,
wherein Alk is an alkyl group of 1-24 carbons in length, and R$_1$ and R$_2$ are independently H or an alkyl group of 1-12 carbons in length. In a particularly preferred embodiment, B=—NH-D, and cosmetic and personal care products including same. Note that the molecules of A (Lys, Arg and His respectively) are shown in their respective charged states at pH 6.0. It is understood that they may be present in an uncharged state as well and the representation of A above is meant to include both.

It has now been discovered that the use of the dipeptides in accordance with the present invention in cosmetic, personal care or dermopharmaceutical compositions can, in many preferred embodiments, enhance anti-aging effects and reduce signs of skin aging considerably. In particular, these cosmetic compositions can be used to treat or prevent wrinkles.

In accordance with the present invention, the term "additive" is distinguished from formulations, personal care products, cosmetics or dermopharmaceutical products. An additive in accordance with the present invention includes a dipeptide or derivative thereof as described herein in combination with certain delivery agents which are useful in performing certain various functions in support of the dipeptides. These functions include, without limitation, solubilizing, dispersing, suspending, structuring, chelating, preserving, stabilizing, adjusting the pH of or protecting from antimicrobial attack the dipeptides.

Generally these additives are not intended to be applied directly to the hair or skin in place of a personal care product, cosmetic or dermopharmaceutical preparation or formulation. Instead, these additives may be supplied to those who manufacture such personal care products, cosmetics or dermopharmaceutical products. From these additives, manufacturers may remove the dipeptide such as by evaporating any included solvent, adding only the dipeptide to, for example, their personal care product. Alternatively, the additive can be measured out so as to provide a sufficient amount of dipeptide for a given formulation and that portion of the additive formulation used as one component in such personal care product. An additive, in accordance with the invention, therefore encompasses something which at least some portion of is added to a personal care product but is not itself a personal care product.

Certain additives in accordance with the present invention can be characterized by the phrase "consisting essentially of." This term is used herein to exclude those things which would materially alter the basic and novel characteristics of the additives. For example, consider a personal care product that will include a chelating agent as well as an additive containing a chelating agent. A chelating agent would not be something which is, in and of itself, contrary to the basic and novel aspects of the invention. However, the amount of chelating agent found in the additive should be sufficient to provide adequate chelation for the dipeptide and/or any other reason to the quality and function of the additive. A suitable excess may also be present. However, in general, the amount of chelating agent present in the additive will not be predicated on the amount necessary for use in the final formulation. If sufficient chelating agent is contained in the additive, that would be a matter of serendipity.

Materials such as humectants, emollients, fragrances and colorings would typically not be included within the phrase "consisting essentially of" unless they served some purpose of enhancing solubility, dispersion, stability, handling or the like of the additive per se. In those instances, they would only be present in an amount which is sufficient to provide those properties and a reasonable excess as appropriate.

The term "dermatologically acceptable" as used herein, means that the compositions or components described are suitable for use in contact with human skin without risk of toxicity, incompatibility, instability, allergic response, and the like. An "effective amount" as used herein means that the content and/or concentration of the dipeptide in the formulation is sufficient that when the formulation is applied with normal frequency and in a normal amount, the formulation can result in the treatment and/or prevention of various signs or symptoms of skin aging and in particular, wrinkles. The amount can also be an amount sufficient to inhibit or enhance some biochemical function occurring within the skin. This amount of dipeptide may vary depending upon the type of product, which of the signs of aging are to be addressed and the like. The formulations of the invention may include an amount of a dipeptide which ranges from about 0.000001 to about 1.0 percent by weight based on the weight of said formulation more preferably, from about 0.00001 to about 0.10 percent by weight based on the weight of said formulation, and most preferably from about 0.0001 to about 0.01 percent by weight based on the weight of said formulation.

All terms such as "skin aging," "signs of skin aging," "topical application," and the like are used in the sense in which they are generally and widely used in the art of developing, testing and marketing cosmetic and personal care products. "Wrinkles" means furrows in the otherwise smooth surface of the facial skin, visible to the naked eye, in the average depth of 50 to more than 200 µm and essentially appearing with progressive age. The term "cosmetic composition" or more briefly just "composition" in accordance with the present invention relates to a formulation that can be used for cosmetic purposes, purposes of hygiene or as a basis for delivery of one or more pharmaceutical ingredients. This includes cosmetics, personal care products and pharmaceutical preparations. It is also possible that these formulations are used for two or more of these same purposes at one time. A medicated dandruff shampoo, for example, has pharmacological properties and is used as a personal care product to provide clean hair. These compositions may also include additional ingredients such as a dermatologically acceptable carrier.

"Cosmetics" as used herein, include without limitation, lipstick, mascara, rouge, foundation, blush, eyeliner, lipliner, lip gloss, facial or body powder, sunscreens and blocks, nail polish, mousse, sprays, styling gels, nail conditioner, whether in the form of creams, lotions, gels, ointments, emulsions, colloids, solutions, suspensions, compacts, solids, pencils, spray-on formulations, brush-on formulations and the like. "Personal care products" include, without limitation, bath and shower gels, shampoos, conditioners, cream rinses, hair dyes and coloring products, leave-on conditioners, sunscreens and sunblocks, lip balms, skin conditioners, cold creams, moisturizers, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, rinses, whether in solid, powder, liquid, cream, gel, ointment, lotion, emulsions, colloids, solutions, suspensions, or other form. "Pharmaceutical preparations" in accordance with the present invention include, without limitation, carriers for dermatological purposes, including topical and transdermal application of pharmaceutically active ingredients. These can be in the form of gels, patches, creams, nose sprays, ointments, lotions, emulsions, colloids, solutions, suspensions, powders and the like. Compositions in accordance with the invention include cosmetics, personal care products and pharmaceutical preparations.

The term "amino acid" as employed herein includes and encompasses all of the naturally occurring and synthetic amino acids, either in the D- or L-configuration if optically active. The term "dipeptide" means a molecule comprising two amino acids as defined herein. "Signs of skin aging" and other phrases similarly referring to, for example, symptoms of aging and the like include, but are not limited to, all outward visibly and tactilely perceptible manifestations as well as any other macro or micro effects due to skin aging. Such signs may be induced or caused by intrinsic factors and/or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin. Particularly preferred in accordance with the present invention, the signs of skin aging are wrinkles and the compositions of the present invention are, in certain preferred embodiments, useful in fighting, treating or preventing wrinkles.

As used herein, prophylactically regulating a skin condition includes delaying, minimizing and/or preventing visible and/or tactile discontinuities in skin (e.g., texture irregularities in the skin which may be detected visually or by feel), including signs of skin aging. This is encompassed within the term "treating."

As used herein, therapeutically regulating skin condition includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition. This is encompassed within the term "treating."

Some of the products and compositions of the present invention are useful for improving skin appearance and/or feel of skin exhibiting signs of skin aging. For example, preferred compositions of the present invention are useful for regulating the appearance of skin conditions by providing an immediate visual improvement in skin appearance following application of the composition to the skin such as a reduction in the apparent width or depth or length of wrinkles to an observer. Generally speaking, compositions of the present invention which further contain particulate materials will be most useful for providing the immediate visual improvement.

Some of the compositions of the present invention may also provide additional benefits, including stability, absence of significant (consumer-unacceptable) skin irritation, anti-inflammatory activity and good aesthetics.

In certain preferred aspects, the present invention is useful for improving the physiological state and/or the physical appearance of human skin, in particular to reduce the signs of skin aging that are generated by sun exposure, physical and hormonal stress, abrasion, nutritional effects and other similar causes. The compositions may often be used to prevent the signs of aging and/or to treat them in order to afford the consumer who uses them, a more youthful appearance.

While the specification concludes with the claims particularly pointing and distinctly claiming the invention, it is believed that the present invention will be better understood from the following description. The terms "having" and "including" are to be construed as open-ended unless the context suggests otherwise.

All percentages and ratios used herein are by weight of the total composition and all measurements made are at 25° C. unless otherwise designated.

The compositions of the present invention can comprise or consist essentially of the components of the present invention as well as other ingredients described herein. As used herein, "consisting essentially of" means that the composition or component may include additional ingredients, but only if the additional ingredients do not materially alter the basic and novel characteristics of the claimed compositions or methods. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained.

In order to implement the invention, it is sufficient to incorporate the active compounds at sufficient and effective concentrations in acceptable cosmetic or dermopharmaceutical compositions and to apply a sufficient and effective quantity to the affected parts of the face, body or hair for a period ranging from 2 weeks to 2 months or more.

In order to enhance the bioavailability and cutaneous barrier crossing of those peptides, their lipophilicity or lipophilic character can be increased either by acylation of the N-terminal $NH_2$ group of the peptide, by esterification of the carboxyl group with an alcohol, linear or branched, saturated or unsaturated, hydroxylated or not, or both.

In preferred methods of implementation of the invention, N-acyl groups used are lauroyl ($C_{12}$) or myristoyl ($C_{14}$) or palmitoyl ($C_{16}$) or stearoyl ($C_{18}$) or oleoyl ($C_{18:1}$) or arachidic ($C_{20}$) or linoleoyl ($C_{18:2}$). Biotinyl groups (biotin or derivatives) are also preferred. In a particularly preferred embodiment, the N terminal group is either H or Palmitoyl.

A "delivery agent" in accordance with the present invention is something which provides benefits to the dipeptide in terms of ease of handling, enhanced storage stability and/or ease of use. These include solvents, dispersants, suspending agents, structuring agents, chelating agents, preservatives, stabilizers, pH adjusters and/or antimicrobial agents. Generally these are selected and provided in an amount which is sufficient to solubilize, disperse, suspend, chelate, preserve, stabilize, adjust the pH of or protect from microbial attack the dipeptides in the additive formulations. Generally, the amount of the delivery agent useful in accordance with the present invention is linked to the amount of dipeptide. In terms of a solvent, for example, the amount of solvent should be an amount necessary to provide the desired level of solubility and may also depend on the volume of the containers in which the additive is to be delivered. In terms of a pH adjusting substance, for example, sufficient acid, base or buffer may be used so as to ensure that the dipeptides of the invention are anionic, cationic or zwitterionic. A suitable excess may be necessary to ensure a particular pH or ionic condition. In terms of an antimicrobial agent, sufficient amount may depend not only on the dipeptide but also on the other ingredients used, the length of storage, the total volume, the manner of storage and the like.

Solvents and solubilisers that are contemplated as delivery agents include, but are not limited to methanol, ethanol, propanol, butanol, isopropanol, pentanol, hexanol, heptanol, octanol, trifluoroethanol, benzyl alcohol, propylene glycol, butylene glycol, glycerine, hexylene glycol and the like; polyethylene glycols; sugars and starches; sugar and starch derivatives; ethoxydiglycol, ethyl-acetate, tetrahydrofurane, dimethylsulfoxide, mp-diol and similar structures;, guanidine; urea; glycolic acid and glycolate salts (e.g. ammonium and quaternary alkyl ammonium); salicylic acid; lactic acid and lactate salts (e.g., ammonium and quaternary alkyl ammonium); polyhydroxy alcohols such as sorbitol, mannitol, xylitol, erythritol, hexanetriol, butanetriol. Also useful herein are the propoxylated glycerols described in U.S. Pat. No. 4,976,953, to Orr et al., issued Dec. 11, 1990.

The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against oxidative degradation of the peptide.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators are EDTA, NTA, gluconic acid, phytic acid, citric acid.

The compositions of the present invention may contain an antimicrobial or antifungal active as a delivery agent. Such actives are capable of destroying microbes, preventing the development of microbes or preventing the pathogenic action of microbes. A safe and effective amount of an antimicrobial or antifungal active may be added to the present compositions, preferably, from about 0.001% to about 1%.

Examples of antimicrobial and antifungal actives include, without limitation phenoxyethanol, phenoxy propanol, phenoxyisopropanol, chlorhexidine, chlorhexidine gluconate, chlorhexidine hydrochloride. Especially useful are combinations with the ingredient range called OSMOCIDE offered by SEDERMA and described in WO 97/05856 of Feb. 20, 1997.

Preferred examples of antimicrobial preservatives useful herein include those selected from salicylic acid, acetyl salicylic acid, phenoxyethanol, phenoxypropanol, phenoxyisopropanol, methyl-, ethyl-, propyl-, butyl- and isoprpoylesters of parahydroxybenzoic acid ("parabens"), chlorphenesine.

Dispersants and suspending agents useful as a delivery agent may include, without limitation, various $C_1$-$C_{30}$ monoesters and polyesters of sugars and related materials. These esters are derived from a sugar or polyol moiety and one or more carboxylic acid moieties. Such ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360, to Volpenhein, issued May 21, 1985. The compositions hereof may contain a structuring agent as a delivery agent. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention contain from about 0.1% to about 20%, more s preferably from about 0.1% to about 10%, still more preferably from about 0.5% to about 9%, of one or more structuring agents.

Suitable structuring agents useful as delivery agents include, without limitation, those selected from saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present invention are selected from stearyl alcohol, cetyl alcohol, behenyl alcohol, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

Thickening Agent (including thickeners and gelling agents) useful as delivery agents may be present preferably from about 0.1% to about 5%, more preferably from about 0.1% to about 4%, and still more preferably from about 0.25% to about 3%, by weight of the composition.

Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; and in CTFA International Cosmetic Ingredient Dictionary, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10\text{-}30}$ alkyl acrylates with one or more monomers of acrylic acid, methacrylic acid, or one of their short chain (i.e., $C_{1\text{-}4}$ alcohol) esters, wherein the crosslinking agent is an allyl ether of sucrose or pentaeryrritol. These copolymers are known as acrylates/$C_{10}$-$C_{30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/$C_{10}$-$C_{30}$ alkyl acrylate-crosspolymers, and mixtures thereof. Especially useful are combinations with the ingredient range called LUBRAJELS offered by UNITED GUARDIAN, some of them described in WO 97/47310 of Jun. 12, 1996.

b) Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al issued Dec. 9, 1986; U.S. Pat. No. 4,599,379 to Flesher et al. issued Jul. 8, 1986; and EP 228,868, to Farrar et al., published Jul. 15, 1987.

c) Polyacrylamide Polymers

The compositions of the present invention can optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc. (Paterson, N.J.).

d) Polysaccharides

A wide variety of polysaccharides are useful herein. "Polysaccharides" refer to gelling agents which contain a backbone of repeating sugar (i.e., carbohydrate) units. Non-limiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkyl-celluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans which are a linear chain of (1-3) linked glucose units with a (1-6) linked glucose every three units, a commercially available example of which is Clearogel™ CS11 from Michel Mercier Products Inc. (Mountainside, N.J.).

e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Preferred compositions of the present invention include as delivery agents a thickening agent selected from carboxylic acid polymers, crosslinked polyacrylate polymers, polyacrylamide polymers, and mixtures thereof, more preferably selected from carboxylic acid polymers, polyacrylamide polymers, and mixtures thereof. pH adjusting substances are acids, bases, buffers, anhydrates, acid halides and the like which can be used to adjust and/or maintain a desired pH. The amount used will depend on the agent and the desired pH.

Generally, the amount of dipeptide in the additives in accordance with the present invention will range from between about 0.0001% to about 99% by weight of the additive, more preferably between about 0.001% and about 10% by weight of the additive. In particularly preferred embodiments the delivery agents will make up the balance.

Just as more than one dipeptide or dipeptide derivative in accordance with the present invention may be provided in an additive in accordance with the present invention, more than one delivery agent may be present. For example, a solvent such as water, a pH adjusting substance such as a buffer and an antimicrobial agent may all be present. The balance of the additive, that which is not dipeptide in accordance with the present invention will generally be composed of these delivery agents, although the amount of each delivery agent may vary significantly with their function in the additive. Generally, more water would be present as a solvent than either an antimicrobial agent or a buffering agent. The amounts of the delivery agents useful may range from: water or other solvent: 0.001%-99.999%, preferably 0.1%-99.9%. Preservative: 0.01%-10%, preferably 0.1%-1%; organic solvents: 0.1%-99.999%, preferably 1%-99%, most preferably 10%-90%; structuring/thickening/gelling/gums: 0.01%-30%, preferably 0.1%-5%; chelating agents: 0.01%-10%, preferably 0.1%-1%.

In one embodiment in accordance with the present invention, additives in accordance with the present invention are provided to a formulator who will remove the dipeptides by various techniques. The dipeptides can then be added to cosmetic and personal care formulations or dermopharmaceutical formulations. In an alternate embodiment in accordance with the present invention, an amount of additive which is sufficient to provide the desired amount of dipeptide is metered out and that amount of the additive, including the desired amount of dipeptide and corresponding amount of delivery agents, is used as one component of a cosmetic, personal care product or dermopharmaceutical formulation.

Additional Ingredients

In addition to the dipeptides, analogs and/or derivatives thereof, and in particular, Lys-Thr, described herein, the compositions of the invention may include various other and additional ingredients, which may be active, functional, conventionally used in cosmetic, personal care or topical/transdermal pharmaceutical products or otherwise. These other ingredients may be formulated with the dipeptides of the invention or the additives which contain same. Of course, a decision to include an additional ingredient and the choice of specific additional ingredients depends on the specific application and product formulation. Also, the line of demarcation between an "active" ingredient and an "inactive ingredient" is artificial and dependent on the specific application and product type. A substance that is an "active" ingredient in one application or product may be a "functional" ingredient in another, and vice versa. A particular ingredient might provide substantivity in one formulation, facilitate transdermal application in another, and merely provide proper viscosity in a third. Which of these is functional and which is active is subject to debate. But, regardless of the outcome, the material in question would qualify as an additional ingredient in accordance with the present invention.

Thus, the compositions of the invention may include one or more additional ingredients, which provide some benefit to the object of the composition. Such additional ingredients may include one or more substances such as, without limitations, cleaning agents, hair conditioning agents, skin conditioning agents, hair styling agents, antidandruff agents, hair growth promoters, perfumes, sunscreen and/or sunblock compounds for hair and/or skin, pigments, moisturizers, film formers, hair colors, make-up agents, detergents, pharmaceuticals, thickening agents, emulsifiers, humectants, emollients, antiseptic agents, deodorant actives, dermatologically acceptable carriers and surfactants.

The compositions of the present invention generally contain at least one additional ingredient. The compositions of the present invention may contain a plurality of additional ingredients as well. Usually these compositions include at least one dermatologically acceptable carrier. In a preferred embodiment, where the composition is to be in contact with human keratinous tissue, the additional ingredients should be suitable for application to keratinous tissue, that is, when incorporated into the composition they are suitable for use in contact with human keratinous tissue (hair, nails, skin, lips) without undue toxicity, incompatibility, instability, allergic response, and the like within the scope of sound medical judgment. The *CTFA Cosmetic Ingredient Handbook*, Tenth Edition (2004) describes a wide variety of nonlimiting cosmetic and pharmaceutical ingredients commonly used in the skin care industry, which are suitable for use as additional ingredients in the compositions of the present invention. Nonlimiting examples of these additional ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof More particularly, additional ingredients include a glycerol, a sorbitol, a pentaerythritol, a pyrrolidone acid and its salts, dihydroxyacetone, erythrulose, glyceraldehyde, tartaraldehyde, a colorant; a water-soluble sunscreen; an antiperspirant, a deodorant, an astringent, a keratolytic, a depilatory, perfumed water, plant tissue extract, a polysaccharide; an anti-dandruff agent; an antiseborrheic agent, an oxidant, a bleaching agent, a reducing agent, a vitamin, a steroid, a hormone, an enzyme, a vaccine, a steroidal or non-steroidal anti-inflammatory, an antibiotic, an antimicrobial, an antibactericidal, a cytotoxic, an antineoplastic agent, fat-soluble active substances selected from the group formed by the fat-soluble sunscreens, substances intended to improve the state of dry or aged skin, tocopherols, vitamins E, F or A and their esters, retinoic acid, antioxidants, essential fatty acids, glycyrthetinic acid, keratolytics and carotenoids, ceramides and pseudo-ceramides, and all lipid complexes of a form similar to that of the natural ceramides of the skin.

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

For the synthesis of the dipeptides of the invention, known peptide chemistry methods and particularly the Fmoc/tBu solid phase method may be used. More chemistry may also be used such as Boc/bzl or liquid phase chemistry.

EXAMPLE 1

Synthesis of Pal-Lys-Thr-OH

Fmoc-Thr(tBu)-OH may be attached on Wang resin. The N-terminal deprotection may be realized with 20% piperidine in DMF. Then the protected Fmoc-Lys(Boc)-OH using DIC/HOBt as reagents. The completion of the reaction is monitored with a ninhydrine test. The protected on resin dipeptide obtained (Fmoc-Lys(Boc)-Thr(tBu)-O-Wang) is deprotected as in the previous step and the fatty acid is coupled in presence of DIC/HOBt to obtain Pal-Lys(Boc)-Thr(tBu)-O-Wang. Cleavage reaction is done in acidic medium (TFA) to regenerate C-terminal and lateral functions. After filtration of the resin, removal of TFA and purification, Pal-Lys-Thr-OH is obtained as a white powder.

Following this general procedure, one should preferably obtain yield 70% having the following general characteristics.

IR: 3299/2917/2850/1635/1583/1541/1462/1399cm-1
Mp: 163-164° C. (decomposition)
HPLC: Conditions : Chromolith C18.5 μm, 1 ml/min, $\lambda$=210 nm, 35° C., inj=5 μl, Conc
1.1 mg/ml MeOH
Gradient: 20-80% ACN /TEAP in 20 min
Ret Time: 17 min

EXAMPLE 2

Quantification of Collagen I and Fibronectin Synthesis Using Human Dermal Fibroblasts.

Products:

Products were tested from 0.5 to 4 ppm depending of their solubility or toxicity. Pal-KTTKS was tested from 2 to 8 ppm.
Solvent=DMSO 0.4%
Pal KTTKS (Lys-Thr-Thr-Lys-Ser), Pal KT (Lys-Thr), Pal KS (Lys-Ser) were prepared in Sederma Peptide Synthesis Laboratory. TGF-beta1: $10^E$-6%, was the positive control for collagen I and Fibronectin studies.

For this study, di-peptides were linked to the Palmitoic acid and were compared to Pal-KTTKS.

Principle:

Normal Human Dermal Fibroblasts (NHDF) were cultivated in culture plates in an appropriate culture medium (i.e. complete DMEM with fetal calf serum). After cell anchorage, cell layers (n=5 replicates) were rinsed with saline buffer and contact with molecules to be tested were performed in a complete DMEM without fetal calf serum. This medium contained ascorbate (sodium salt) and beta-aminopropionitrile, monofumarate. Two independent experimentations were performed for each di-peptide.

After 3 days of incubation, supernatants were collected and frozen. Survival was estimated on cell layer using the fluorescent probe Hoescht 33258. Collagen I was estimated using an original direct ELISA method. Fibronectin was estimated using ELISA commercial kit.

Results:
Criteria: TGF-b1 should be promoter of Collagen I and Fibronectin synthesis. Statistical analysis were performed on Collagen I data (n=5/assay) or Fibronectin data (n=5/assay). Results obtained with molecules were compared to negative control. All data were ng/$10^E6$ cells. A Student t test for non paired values was used; significativity was obtained if p<0.05 or p<0.01.

TABLE 1

Effect of various peptide4 sequences on NHDF's Collagen I and Fibronectin ssynthesis. Results are in percent of negative control.

| Product | Concent. | | COLLAGEN I Mean | FIBRONECTIN Mean |
|---|---|---|---|---|
| TGF-beta | 10 | ppb | +95% | +69% |
| Pal KTTKS | 2 | pppm | +5% | +20% |
|  | 4 | pppm | +49% | +25% |
|  | 6 | pppm | +111% | +39% |
|  | 8 | ppm | +144% | +64% |
| Pal KT | 1 | pppm | +21% | +29% |
|  | 2 | pppm | +35% | +32% |
|  | 4 | pppm | +59% | +34% |
| Pal KS | 0.5 | pppm | −10% | +3% |
|  | 1 | pppm | 0% | +11% |
|  | 2 | pppm | +7% | +10% |
|  | 4 | ppm | Precipitated | Precipitated |

The percents in the tables above were calculated from ng/10E6 data and compared to the negative control.

As usual, TGF-b1 shows a significant increase of cell proliferation after 3 days of culture.

Collagen I:
The TGF-b1 always shows a significant (p<0.01) increase in collagen I synthesis, demonstrating that the cells respond correctly to stimulation (from +14% to +184%). A mean increase of 95% can be observed.

Pal-KTTKS considered as a benchmark, has a dose-response effect from 4 to 8 ppm (+49% (p<0.05), +111% (p<0.01) & +144% (p<0.01) of increase in collagen I synthesis for 4, 6 & 8 ppm respectively). The number of cells is unchanged after 3 days of culture.

The Pal KT shows a significant increase in collagen I synthesis at 4 ppm (+59%). It is probably positive at 2 ppm. Pal KT is as efficient as Pal-KTTKS at 4 ppm The Pal KS does not increase collagen I synthesis. At 4 ppm, Pal KS precipitated and seemed to induce a light toxicity.

Fibronectin:
The TGF-b1 always shows a significant (p<0.01) increase in fibronectin synthesis, demonstrating that the cells respond correctly to stimulation (from +55% to +83%). A mean increase of 69% can be observed.

Pal KTTKS considered as a benchmark, presents an increase of fibronectin from 4 to 8 ppm (+25% (p<0.05), +39% (p<0.05) & +64% (p<0.01) for 4, 6 & 8 ppm respectively). At 2 ppm Pal KTRKS is probably active.

The Pal KT shows a significant increase in fibronectin synthesis at 1 ppm (+29%), 2 ppm (+32%), and 4 ppm (+34%). It is more efficient than Pal-KTTKS at 2 and 4 ppm.

The Pal KS does not increase fibronectin synthesis. At 4 ppm, Pal KS precipitated and seemed to induce a light toxicity.

The invention claimed is:

1. A dipeptide having the following structure:

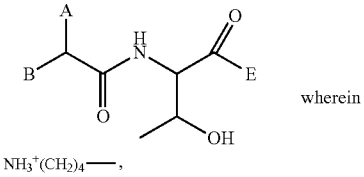

wherein $A = NH_3^+(CH_2)_4$—,

B=—NH-D,
D=an acyl group of 16 carbon atoms in length, and
E =—OH.

2. An additive for use in personal care products comprising: at least one dipeptide having the following structure

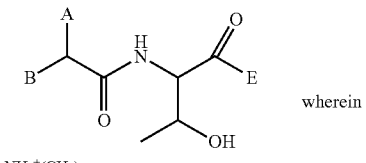

wherein $A = NH_3^+(CH_2)_4$—,

B=—NH-D,
D=an acyl group of 16 carbon atoms in length, and
E=—OH, and
at least one delivery agent.

3. The additive of claim 2, wherein said delivery agent is, a solvent, dispersant, suspending agent, structuring agent, chelating agent, preservative, stabilizer, pH adjuster or antimicrobial agent.

4. The additive of claim 3, wherein said dipeptide is provided in an amount of between about 0.0001% and about 99% by weight of said additive.

5. The additive of claim 4, wherein said dipeptide is provided in an amount of between about 0.001% and about 10% by weight of said additive.

* * * * *

UNITED STATES PATENT AND TRADEMARK OFFICE
CERTIFICATE OF CORRECTION

PATENT NO.      : 7,977,308 B2                                          Page 1 of 1
APPLICATION NO. : 11/919539
DATED           : July 12, 2011
INVENTOR(S)     : Karl Lintner It is certified that error appears in the above-identified patent and that said Letters Patent is hereby corrected as shown below:

Column 9, line 40, "more s preferably" should read --more preferably--.
Column 13, line 46, "thereof More" should read --thereof. More--.
Column 16, line 22, claim 1 should read:
    B = –NH-D,
    D = an acyl group of 16 carbon atoms in length, and
    E = –OH.
Column 16, line 37, claim 2 should read:
    B = –NH-D,
    D = an acyl group of 16 carbon atoms in length, and
    E = –OH, and
Column 16, line 42, claim 3, "is, a" should read --is a--.

Signed and Sealed this
Tenth Day of July, 2012

David J. Kappos
*Director of the United States Patent and Trademark Office*